(12) United States Patent
Fruland et al.

(10) Patent No.: US 8,105,003 B2
(45) Date of Patent: Jan. 31, 2012

(54) METHOD AND APPARATUS FOR A FASTENER AND A FASTENER COVER INCLUDING A SEALABLE OPENING

(75) Inventors: Benjamin R. Fruland, Plymouth, MN (US); Kevin J. Persuitti, Andover, MN (US); Scott Dahl, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 885 days.

(21) Appl. No.: 11/622,308

(22) Filed: Jan. 11, 2007

(65) Prior Publication Data
US 2008/0063490 A1  Mar. 13, 2008

Related U.S. Application Data

(60) Provisional application No. 60/825,052, filed on Sep. 8, 2006.

(51) Int. Cl.
*A47G 3/00* (2006.01)
(52) U.S. Cl. .................. 411/377; 411/360; 411/393
(58) Field of Classification Search ............ 607/36–38, 607/1–2; 411/360, 372.5–373, 377, 393, 411/999
See application file for complete search history.

(56) References Cited

U.S. PATENT DOCUMENTS

| | | | |
|---|---|---|---|
| 4,037,277 A | | 7/1977 | Shipko |
| 4,262,673 A | | 4/1981 | Kinney et al. |
| 4,316,471 A | * | 2/1982 | Shipko et al. ............ 607/37 |
| 4,461,194 A | * | 7/1984 | Moore ........................... 81/436 |
| 4,479,489 A | * | 10/1984 | Tucci ............................ 607/37 |
| 4,832,021 A | | 5/1989 | Kuhl et al. |
| 4,932,409 A | * | 6/1990 | Hirschberg ................... 607/36 |
| 4,942,876 A | | 7/1990 | Gotthardt |
| 5,000,177 A | | 3/1991 | Hoffmann et al. |
| 5,413,595 A | | 5/1995 | Stutz, Jr. |
| 5,486,202 A | | 1/1996 | Bradshaw |
| 5,509,928 A | * | 4/1996 | Acken ........................... 607/37 |

(Continued)

FOREIGN PATENT DOCUMENTS
EP    0052690 A1    6/1982
(Continued)

OTHER PUBLICATIONS

"International Application Serial No. PCT/US2007/019603, International Search Report mailed Jul. 31, 2008", 7 pgs.

(Continued)

*Primary Examiner* — Victor Batson
*Assistant Examiner* — Roberta Delisle
(74) *Attorney, Agent, or Firm* — Schwegman, Lundberg & Woessner, P.A.

(57) ABSTRACT

One embodiment of the present subject matter includes a system for fastening a male terminal with a driver. The embodiment includes a body defining an at least partially threaded recess which intersects with a female recess adapted to receive the male terminal. The embodiment additionally includes a fastener having an at least partially threaded body and a flanged head adapted to mate with the driver, the fastener disposed at least part of the way in the first recess, the flange having a diameter which is larger than a diameter of the at least partially threaded recess. The embodiment includes a flexible septum coupled to the body and covering the first recess, the flexible septum having an opening sized for passage of the driver.

21 Claims, 3 Drawing Sheets

U.S. PATENT DOCUMENTS

| | | | |
|---|---|---|---|
| 5,707,399 | A | 1/1998 | Killander et al. |
| 5,738,664 | A | 4/1998 | Erskine et al. |
| 5,766,042 | A | 6/1998 | Ries et al. |
| 5,951,595 | A | 9/1999 | Moberg et al. |
| 5,989,077 | A * | 11/1999 | Mast et al. ............... 439/814 |
| 6,029,089 | A | 2/2000 | Hawkins et al. |
| 6,053,861 | A | 4/2000 | Grossi |
| 6,059,786 | A | 5/2000 | Jackson |
| 6,080,188 | A | 6/2000 | Rowley et al. |
| 6,128,984 | A | 10/2000 | Haupt |
| 6,162,206 | A | 12/2000 | Bindokas et al. |
| 6,212,434 | B1 | 4/2001 | Scheiner et al. |
| 6,390,843 | B1 | 5/2002 | Lim |
| 6,540,666 | B1 | 4/2003 | Chekanov |
| 7,155,283 | B2 * | 12/2006 | Ries et al. ............... 607/37 |
| 7,187,974 | B2 * | 3/2007 | Haeg et al. ............... 607/36 |
| 7,231,253 | B2 * | 6/2007 | Tidemand et al. ......... 607/37 |
| 7,305,267 | B2 * | 12/2007 | Hector ...................... 607/37 |
| 2003/0088151 | A1 | 5/2003 | Kung |
| 2004/0215282 | A1 * | 10/2004 | Weijden et al. ............ 607/37 |
| 2006/0009672 | A1 | 1/2006 | Verma |
| 2006/0015063 | A1 | 1/2006 | Butikofer et al. |
| 2006/0259092 | A1 | 11/2006 | Spadgenske et al. |
| 2007/0213781 | A1 * | 9/2007 | Fruland et al. ............. 607/37 |
| 2010/0016861 | A1 | 1/2010 | Fruland et al. |

FOREIGN PATENT DOCUMENTS

| | | |
|---|---|---|
| WO | WO-03/007778 A2 | 1/2003 |
| WO | WO-2004/066805 A2 | 8/2004 |
| WO | WO-2008/030593 A2 | 3/2008 |
| WO | WO-2008/030593 C1 | 3/2008 |

OTHER PUBLICATIONS

"International Application U.S. Appl. No. PCT/US2007/019603, Written Opinion mailed Jul. 31, 2008", 9 pgs.

"European Application Serial No. 07837935.1, Office Action mailed Nov. 24, 2009", 4 pgs.

"U.S. Appl. No. 11/276,699, Examiner Interview Summary mailed Jun. 21, 2010", 1 pg.

"U.S. Appl. No. 11/276,699, Final Office Action mailed Mar. 8, 2010", 10 pgs.

"U.S. Appl. No. 11/276,699, Non-Final Office Action mailed Jun. 10, 2009", 11 pgs.

"U.S. Appl. No. 11/276,699, Non-Final Office Action mailed Jun. 21, 2010", 11 pgs.

"U.S. Appl. No. 11/276,699, Non-Final Office Action mailed Sep. 30, 2008", 12 pgs.

"U.S. Appl. No. 11/276,699, Response filed Feb. 26, 2009 to Non-Final Office Action mailed Sep. 30, 2008", 15 pgs.

"U.S. Appl. No. 11/276,699, Response filed Jun. 8, 2010 to Final Office Action mailed Mar. 8, 2010", 16 pgs.

"U.S. Appl. No. 11/276,699, Response filed Sep. 10, 2009 to Non-Final Office Action mailed Jun. 10, 2009", 14 pgs.

"U.S. Appl. No. 11/276,699, Response filed Sep. 20, 2010 to Non-Final Office Action mailed Jun. 21, 2010", 16 pgs.

"European Application Serial No. 07837935.1, Office Action mailed Jul. 15, 2010", 6 pgs.

"European Application Serial No. 07837935.1, Reply filed Mar. 29, 2010 to Communication mailed Nov. 24, 2009", 8 pgs.

"MED-420 Silicone Fluid Product Profile", NuSil Technology, Carpinteria, CA, (Mar. 2009), 3 pgs.

"U.S. Appl. No. 11/276,699, Final Office Action mailed Dec. 8, 2010", 11 pgs.

"European Application Serial No. 07837935.1, Office Action mailed Jan. 25, 2011", 4 pgs.

"European Application Serial No. 07837935.1, Response filed Nov. 19, 2010 to Office Action mailed Jul. 16, 2010", 9 pgs.

"Japanese Application Serial No. 2009-527440, Amended Claims filed Aug. 4, 2010", (w/English Translation of Amended Claims), 9 pgs.

"European Application Serial No. 07837935.1, Response filed Aug. 3, 2011 to Office Action mailed Jan. 25, 2011", 9 pgs.

* cited by examiner

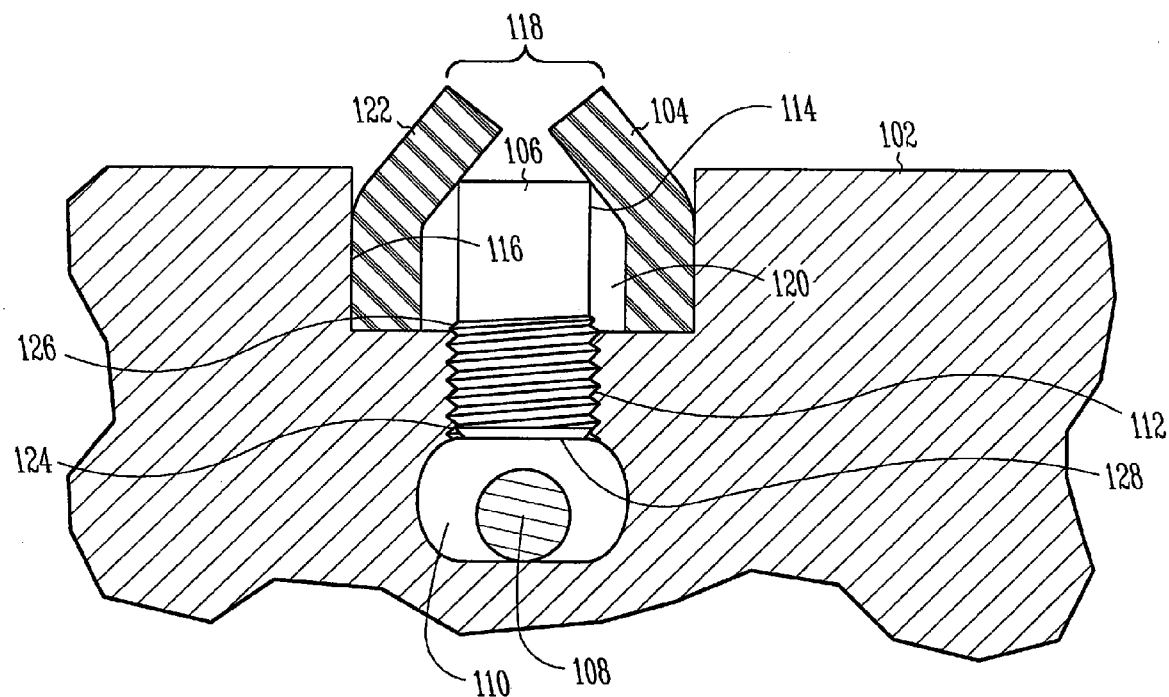
*Fig. 1A (SIDE VIEW)*
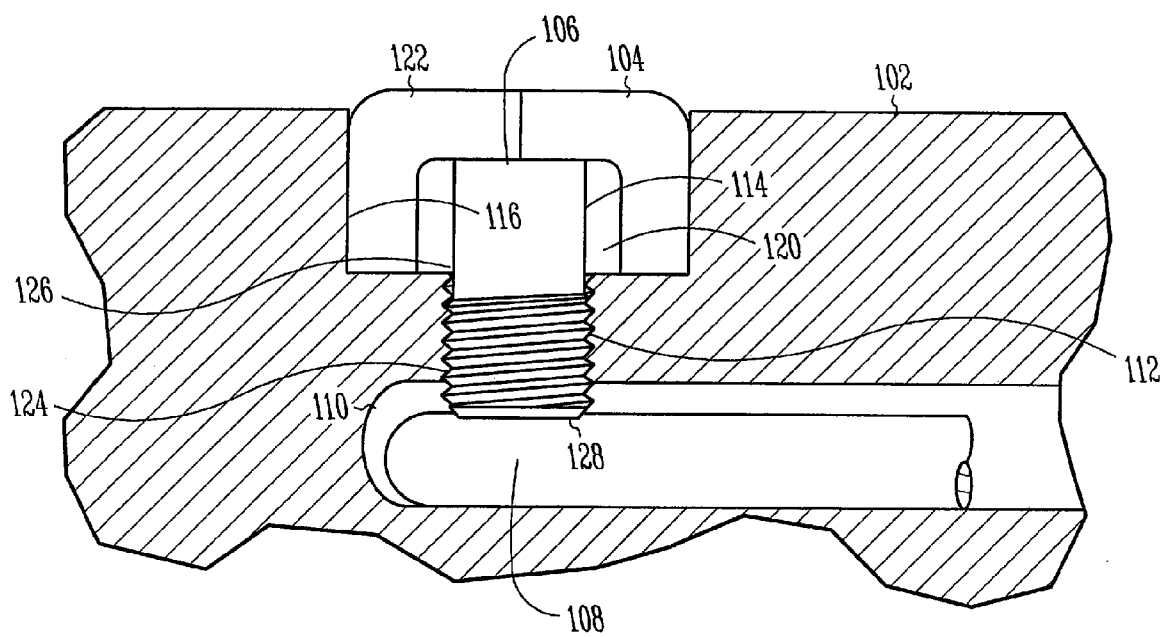
*Fig. 1B (FRONT VIEW)*

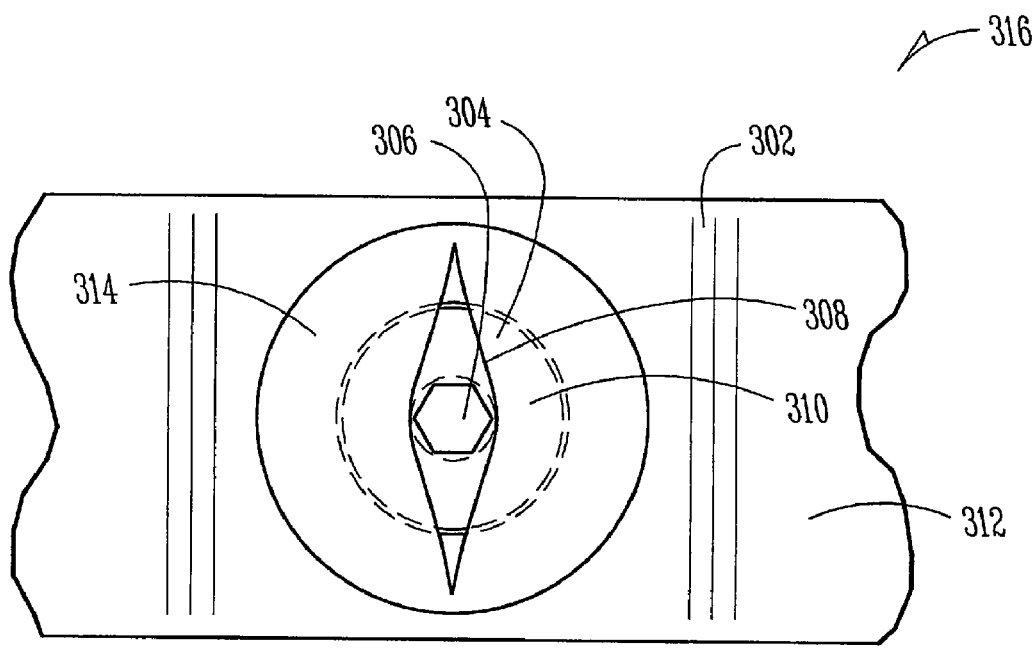
Fig. 3B
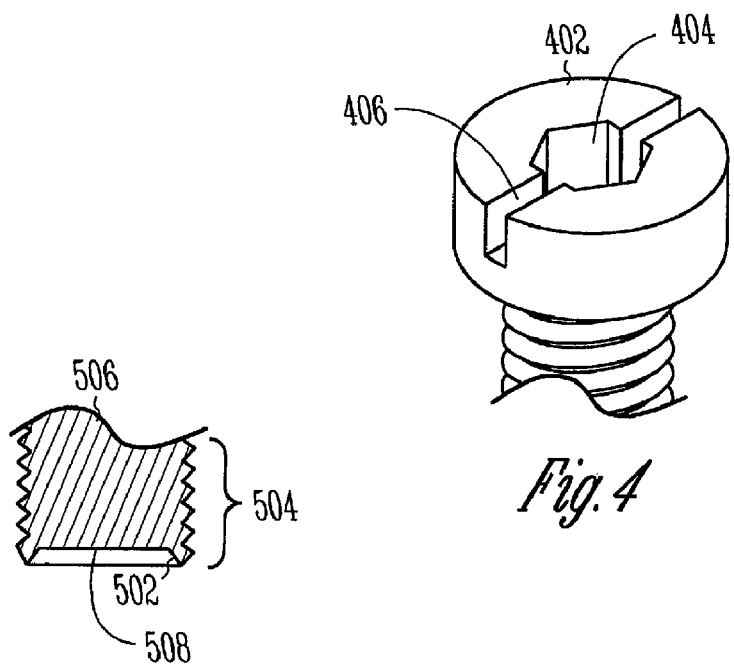
Fig. 4
Fig. 5

METHOD AND APPARATUS FOR A FASTENER AND A FASTENER COVER INCLUDING A SEALABLE OPENING

CROSS REFERENCE TO RELATED APPLICATION

This application claims the benefit of U.S. Provisional Application No. 60/825,052, filed on Sep. 8, 2006, under 35 U.S.C. §119(e), which is hereby incorporated by reference.

TECHNICAL FIELD

This disclosure relates generally to fasteners, and more particularly to a method and apparatus for a fastener with a septum seal cover.

BACKGROUND

There is an ongoing need to provide devices which can be exposed to fluids without malfunctioning. Some designs cannot simply be encased in a fluid compatible, sealed material, as they must be manipulated in use. Such is the case with some devices which are implanted in a person. Some implantable systems include interchangeable components which conduct electricity. For example, some designs use a set fastener to pinch a lead. Devices such as these must provide reliable electrical and mechanical connection which does not degrade in use.

Various problems are associated with such designs. Bodily fluids can reduce the operability of these devices by binding components to one another. As such, workers have attempted to provide covers for these devices. However, many covers which provide good sealing characteristics, such as silicone covers, present a problem of bonding to other components, or to themselves, in use and in storage.

An additional problem is that a fastener can become misaligned, or skew to their mating feature, during surgery. Further, some fastener designs encourage cross threading, especially when a doctor is inserting a driver through a seal. When inserting a driver through a seal, it is important to have the fastener in alignment with the seal opening; some designs do not encourage this. An additional problem is that some fastener designs can crush and damage the leads they pinch.

SUMMARY

One embodiment of the present subject matter includes a system for fastening a male terminal with a driver. The embodiment includes a body defining an at least partially threaded recess which intersects with a female recess adapted to receive the male terminal. The embodiment includes a fastener having an at least partially threaded body and a flanged head adapted to mate with the driver, the fastener disposed at least part of the way in the first recess, the flange having a diameter which is larger than a diameter of the at least partially threaded recess. The embodiment includes a flexible septum coupled to the body and covering the first recess, the flexible septum having an opening sized for passage of the driver. In the embodiment, a first mode of operation, the system is adapted to clamp the male terminal between the body and the fastener, with the opening closed and sealed, and in a second mode of operation the system is adapted to not clamp the male terminal between the body and the fastener while the flange abuts the flexible septum such that the opening is open and unsealed.

Another embodiment is contemplated which provides a method storing an implantable device. The embodiments includes assembling a fastener into a recess in a body of the implantable device, the recess being covered by a flexible septum having a slit. The embodiment further includes opening the slit by adjusting the fastener with respect to the device such that a flange of the fastener abuts the flexible septum. The embodiment includes packaging the implantable device for storage. The embodiment further includes storing the implantable device.

One embodiment of the present subject matter includes body means for receiving a fastener and a male terminal. The embodiment includes fastener means for securing the male terminal to the body means, for limiting the travel of the fastener into the body means, and for preserving alignment of the fastener means with respect to the body means when the male terminal is not secured to the body means. The embodiment further includes cover means for covering the fastener and for sealing the fastener means and the body means.

The present subject matter includes optional features in additional embodiments. Some of those embodiments include a fastener which is part of a cardiac rhythm management device, such as a pacemaker or a defibrillator. Some embodiments include a silicone cover. Some embodiments include a fastener having a convex distal portion. Some embodiments include a fastener mateable to a male hex driver. Embodiments include taking a device out of storage and inserting a male terminal into the device, and securing that terminal to the device using a fastener of the present subject matter. Openings in covers of the present subject matter are lubricated, in various embodiments. Other options are disclosed herein.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIG. 1A illustrates a cross section of a fastener and a lead in an unfastened position, according to one embodiment of the present subject matter.

FIG. 1B illustrates a cross section of a fastener and a lead in a fastened position, according to one embodiment of the present subject matter.

FIG. 3B illustrates a top view of the view in FIG. 3A.

FIG. 4 illustrates a partial perspective view of a fastener, according to one embodiment of the present subject matter.

FIG. 5 illustrates a partial cross section of a fastener, according to one embodiment of the present subject matter.

DETAILED DESCRIPTION

Figure 2:
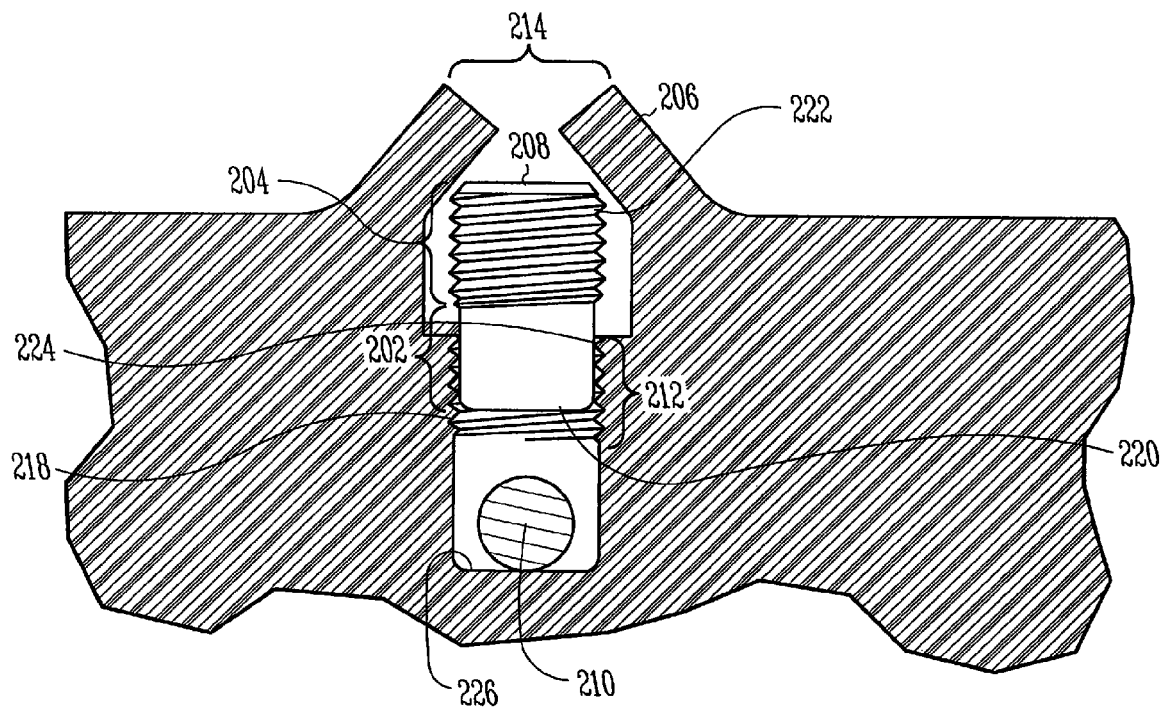
FIG. 2 illustrates a cross section of a fastener and a lead in a lead unfastened position, according to one embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter provides a connector for connecting a terminal of one component of a system to another component of a system. The terminals are male and female. In various embodiments, the present subject matter provides a first terminal for connection of an implantable lead to a second terminal which is part of an implantable device. Devices contemplated include, but are not limited to, cardiac rhythm management electronics including, but not limited to, pacemakers, defibrillators, cardioverter defibrillators. The present subject matter additionally contemplates other devices which deliver an electrical pulse to the body. Additional devices beyond these also benefit from features disclosed herein. In various embodiments, the terminal for the lead is male, although the present subject matter is not so limited. Among the embodiments contemplated are those in which a fastener is threaded into a device such that the fastener may encroach into a recess of a female terminal of a device. As the fastener is tightened, it pinches against a male terminal inserted into the female terminal, in various embodiments. The present subject matter contemplated embodiments in which the female terminal is a portion of a lead, and the male terminal is a portion of the device.

The present subject matter covers a range of fastener embodiments. Some embodiments contemplated include threads. Additional embodiments contemplated include fasteners which include a shaft with grooves which are adapted to mate with pins in a recess such that rotation of the fastener with respect to the recess receives the pins in the grooves and draws the fastener into the recess. Some of these embodiments limit the radial motion of the fastener. For example, fasteners contemplated by the present subject matter go from being uncoupled to a recess at 0 degrees rotation, to fully coupled with a recess at 270 degrees rotation. Some of these embodiments provide tactile feedback so a fastener operator can feel when the fastener is fully engaged. Some embodiments provide features in the grooves of the fastener, such as ribs, which provide additional feedback. Such features additionally may discourage disengagement of the fastener from the recess.

Some embodiments of the present subject matter provide a cover for the fastener. Various embodiments include a septum which covers the fastener. In some of these embodiments, the septum provides at least a partial seal against bodily fluids. In some embodiments, the septum includes an opening through which a driver can be inserted to adjust the fastener.

Various embodiments of the present subject matter provide an improved fastener. Some embodiments provide a fastener with a flanged head such that the fastener cannot be fastened into a fastener hole beyond a predetermined depth. These embodiments work to reduce damage to a male terminal during tightening of the fastener. The flange serves additional functions as well. Some of these are discussed herein.

Some embodiments provide a fastener having an unthreaded portion which extends away from the threads and leads the fastener into a mating fastener hole. These embodiments reduce instances of the fastener tipping, or become skew with respect to its mating recess, after it is disengaged from its recess. These embodiments additionally reduce instances of a fastener going out of alignment with an access opening in a cover which covers the fastener.

In various embodiments, materials which bond to themselves or which bond to other objects over time are provided. For example, in some embodiments, a silicone cover is provided with an opening in it for accessing a fastener of the present subject matter. In various embodiments, the fastener helps to keep an opening of a cover open so that the opening does not stick close or bond closed. In various embodiments, the fastener keeps an opening of the cover open in storage. In some embodiments, the flanged head of the fastener keeps the opening open. In some embodiment, the opening is a slit, and is shaped to work in conjunction with the fastener to open when the fastener is backed out of the recess.

FIG. 1A illustrates a cross section of a fastener and a lead in an unfastened position, according to one embodiment of the present subject matter. FIG. 1B illustrates a cross section of a fastener and a lead in a fastened position, according to one embodiment of the present subject matter. The illustrated fastener 106 is a set screw, but the present subject matter is not so limited, as other fasteners, including fasteners having a head, are contemplated by the present subject matter.

Various embodiments of the present subject matter provide a system for fastening a fastener 106 with a driver. Drivers contemplated by the present subject matter include a range of interfaces. In interfaces contemplated by the present subject matter include, but are not limited to, hex socket, hex head, TORX, slot, PHILLIPS, and/or combinations thereof. This list is not exhaustive or exclusive of the present subject matter, and additional fasteners designs are also contemplated. TORX is a registered trademark of Textron, Inc., which is incorporated in Delaware and has an office at 40 Westminster Street in Providence, R.I. 02903. PHILLIPS is a registered trademark of Phillips Screw Company, which is incorporated in Delaware and has an office at 8 Mercer Road in Natick, Mass. 01760. In some embodiments of the present subject matter, the driver provides the male interface, and the fastener provides the female interface. Additional embodiments are contemplated in which the driver includes the female interface, and the fastener includes the male interface. Additional drives which engage fasteners using techniques not expressly disclosed here are also contemplated.

Various embodiments of the present subject matter provide a body 102 defining an at least partially threaded recess 112 for a fastener. In various embodiments, the recess 112 includes a distal portion 124 and a proximal portion 126. Bodies which are contemplated by the present subject matter include housings for implantable devices, as well as feedthroughs or headers which are attached to one or more additional devices. Some of these embodiments provide a body 102 which seals its contents. For example, some bodies seal housed electronics from the encroachment of bodily fluids.

In various embodiments, the recess intersects with a female recess 110 adapted to receive the male terminal 108. Various male terminals are contemplated by the present subject matter, including male terminals for leads. Male terminals for sensors and for stimulation electrodes which are not on a lead are also contemplated. Other components having a male terminal are additionally compatible with the present subject matter. Although the illustrated embodiments shows a lead with a male terminal, and a body with a female terminal, the present subject matter is not so limited, and embodiments which are configured otherwise are additionally contemplated. For example, various embodiments include a body having a male terminal which is configured to mate with a female terminal conducted to one or more devices. In some of these embodiments, the female terminal is connected to a lead.

In various embodiments, a male terminal 108 is inserted into the female terminal, and is pinched. In some of these embodiments, pinching is performed by twisting a driver coupled to the fastener. In various embodiments, the driver is torque limited. In additional embodiments, the driver is not torque limited.

Various embodiments of the present subject matter include a cover 104 for the fastener 106. In some embodiments, the cover 104 is integrated with the body 102. Some of these embodiments provide a polymer body 102 and cover 104. This configuration is one embodiment contemplated by the present subject matter. Additional embodiments, in which the cover 104 is not integrated with the body 102 are contemplated as well.

In various embodiments, the fastener 106 includes a proximal portion 114 and a distal portion 128. In various embodiments, recess 116 is an opening countersunk into body 102. In some of these embodiments, the recess 116 is cylindrical, but other shapes are possible. In embodiments having such a recess, various embodiments include a cover 104 which is fit into recess 116. In various embodiments, the cover 104 is a plug which is interference fit into recess 116. In various embodiments, the interference fit includes additional features, such as ribs, threads, teeth, or other fastening features. In various embodiments, the fit of cover 104 into recess 116 is such that the fastener 106 can open an opening 118 in cover 104 without unseating the cover 104 from the recess 116.

In various embodiments, the cover 104 defines a septum which defines a chamber 120 under which fastener 106 is disposed. Such a relationship, in various embodiments, reduces instances of encroachment of fluids into chamber 120. Although the pictured embodiment includes a chamber 120 which is larger than the fastener 106, the present subject matter is not so limited and includes chambers which are form fitting to the fastener. Such designs can reduce the size of a device. In implanted embodiments, this can result in improved patient comfort. In various embodiments, this can also result in easier implantation procedures for care givers.

In various embodiments, the septum is flexible. In various embodiments, the septum includes silicone. In additional embodiments, the septum is another polymer, or a combination of another polymer and silicone. This is not an exhaustive or exclusive list of the present subject matter, and additional materials are contemplated.

In various embodiments, the septum includes an opening sized for passage of a driver. Some embodiments of the present subject matter include a septum having an opening sized for passage of a hex head driver mateable to the fastener 106. In various embodiments, the opening is sized such that the driver may pass through the opening without tearing or otherwise harming the opening.

In various embodiments, the present subject matter provides a first mode of operation. One of these embodiments is depicted in FIG. 1B. In that mode, a system of the present subject matter clamps the male terminal between the body and the fastener, with the opening closed and sealed. Some sealed embodiments provide a seal which resists flow of bodily fluids. Additional seals within the scope of the present subject matter do not resist the flow of bodily fluids, but otherwise provide a seal. Examples of such seals are seals which keep out dust. Other seals are additionally contemplated by the present subject matter.

The present subject matter provides a second mode of operation, in various embodiments. One of these embodiments is depicted in FIG. 1A. The second mode includes a system of the present subject matter which does not clamp the male terminal between the body and the fastener. This second mode, in various embodiments, includes a fastener 106 which abuts the septum 122 such that the opening is open and unsealed. In various embodiments, the opening 118 is a shaped like a slit in the cover 104. The present subject matter includes openings having additional shapes as well, such as circular holes adapted to seal unto themselves.

In various embodiments, the fastener 106 is radioopaque. In some of these embodiments, care givers are able to better determine the orientation of an implantable device with respect to a patient. An additional benefit is that the engagement of the male terminal with the female terminal can be studied without explant. This is not an exhaustive or exclusive list of benefits provided.

FIG. 2 illustrates a cross section of a fastener 208 and a lead 210 in a lead unfastened position, according to one embodiment of the present subject matter. A cover 206 is provided. In the illustration, the cover is flexed such that an opening 214 is demonstrated. In various embodiments, the opening 214 is large enough for the fastener 208 to pass through. In various embodiments, a driver which can couple with the fastener and apply a torque the fastener is contemplated.

The fastener 208 illustrated is one of a range of embodiments which are partially threaded. The fastener includes a proximal end 222 and a distal end 220. The fastener includes a threaded portion 204 and an unthreaded portion 202. In various embodiments, the fastener is partially engaged with the recess 218. The recess 218 includes a proximal end 224 and a distal end 226. In various embodiments, the unthreaded portion 202 extends into the recess and at least partially engages the recess 218. One or more threads of the fastener 208 may engage one or more threads of the recess 218, in various embodiments.

In some of the embodiments in which the threaded portion of the fastener 208 is not fully threaded into the recess 218, a device operator is extracting fastener 208 from the recess 218. An operator may seek to perform such an operation for various reasons. One reason is that a care giver might want to explant a first device to replace it with a second device. The care giver may want to mate the lead of the first device to the second device. Other reasons additionally contemplated. In these situations, the care giver backs the fastener 208 out of the recess 218 using multiple turns with a driver. In some of these embodiments, the care giver backs the fastener 208 out of the recess 218 until no threads of the fastener 208 engage threads of the recess 218. In embodiments which do not include a threaded portion 212 of the fastener 208, the fastener 208 might tip or otherwise go out of alignment with the recess 218, making reinsertion of the fastener 208 into the recess 218 more difficult. Embodiments of the present subject matter address this issue. Embodiments may additionally address issues not recited herein expressly.

Some embodiments of the present subject matter reduce the need to include features in recess 218 which stop the progress of fastener 208 as it is positioned within recess 218. For example, some embodiments of the present subject matter which do not include unthreaded portion 220 can tip upon extraction from the recess 218. As such, in some embodiments, a fastener is fully disposed in a recess. A stopper is then inserted near the proximal end 224 of the recess such that the fastener cannot be removed easily from the recess 218, in various embodiments. One example of a stopper is a washer welded into recess 218, but other embodiments are contemplated. These embodiments present an issue when an operator uses excessive torque in an attempt to overcome the stopper without realizing that the stopper is impeding the progress of the extraction of the fastener from the recess. The issue is that the stopper and the fastener can become wedged together. To reduce instances of wedging, the present subject matter provides an unthreaded portion 212 to reduce instances of tipping.

Figure 3A:
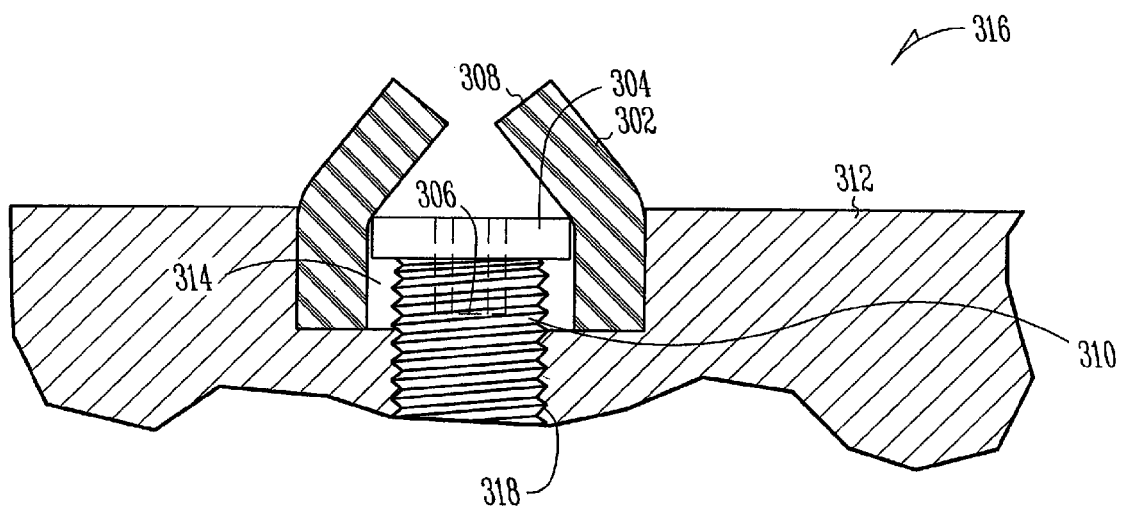
FIG. 3A illustrates a partial side view of a cross section of a fastener in an unfastened position, according to one embodiment of the present subject matter.

FIG. 3A illustrates a partial side view of a cross section of a fastener in an unfastened position, according to one embodiment of the present subject matter. FIG. 3B illustrates a top view of the view in FIG. 3A. Various embodiments include a fastener 310 which is fastened to body 312. In various embodiments, the fastener includes a flanged portion 304. The fastener additionally includes a recess 306 mateable to a driver, in various embodiments. In additional embodiments, the fastener is a hex head fastener. Embodiments are contemplated in which the fastener 310 does not include a recess 306 and is actuated another way.

Various embodiments include a cover 302. In some of these embodiments, the cover 302 has a slit 308. In various embodiments, the slit is closeable such that it seals a chamber 314. In some embodiments, the chamber 314 is sealed from the encroachment of bodily fluids into the chamber 314.

In some embodiments, the cover 302 is manufactured from silicone. Over prolonged periods of time, two pieces of silicone can partially or fully bond together when put into contact with one another. As such, the present subject matter provides an operator of the fastener 310 the option to store device 316 with the fastener configured as illustrated in FIG. 3A. The fastener includes a flange 304 which is oversized, having a large diameter than the diameter of the recess 318. This allows for various functions. One function is to hold open an opening in the cover 302 so that silicone does not bond with itself. Another function is to limit the travel of the fastener 310 into the recess 318. Such a limit can protect against crushing of a male terminal which the fastener 310 cinches against the body 312. In some embodiments, if a fastener system can protect against crushing, device 316 sellers do not have to package the device with a torque limited driver. Further, reducing instances of crushing can reduce the need to train operators on how to avoid crushing a terminal while operating fastener 310. Another benefit of the present subject matter is that the opening in the cover 302 provides a visual cue that the fastener 310 is not yet inserted into the recess 318.

FIG. 4 illustrates a partial perspective view of a fastener, according to one embodiment of the present subject matter. The fastener 402, in various embodiments, includes a recess 404. In some of these embodiments, the recess 404 is a hex socket, as pictured. Embodiments of the present subject matter additionally include a slot 406, either alone, or in combination with another feature suited for coupling fastener 402 with a driver. Embodiments may additionally include other features as disclosed herein.

FIG. 5 illustrates a partial cross section of a fastener, according to one embodiment of the present subject matter. Illustrated is a fastener 506, according to some embodiments of the present subject matter. The illustrated cross section is the distal portion of a fastener 506. The fastener includes a threaded portion 504. Additional embodiments are not threaded. In various embodiments, the distal end of the fastener 506 is substantially convex. In some embodiments, the substantially convex feature includes a substantially planar portion 508 and a bevel 502. Additional shapes are possible, however, including a partial sphere shape, in some embodiments.

Various processes are contemplated by the present subject matter. Some embodiments of the present subject matter include a method storing an implantable device. Some of these embodiments include assembling a fastener into a recess in a body of the implantable device. In some embodiments, the recess is covered. In some of these embodiments, the recess is covered by a flexible septum.

In some embodiments, the septum has an opening. In some of these embodiments, the opening is a slit. In some embodiments, the slit may be opened by adjusting the fastener with respect to the device. In some embodiments, the fastener backs into the septum and forces the slit open. In some embodiments, the fastener includes a flange which aids in opening the slit. In some embodiments including a flange, the flange of the fastener abuts the flexible septum. The flange additionally prevents overtorquing of the fastening during tightening, in various embodiments.

Some embodiments include packaging the implantable device for storage. Some embodiments include storing the implantable device. Storage practices contemplated include, but are not limited to, warehousing, storing with a reseller, storing with a sales person, and other storing practices not recited herein expressly.

An additional process contemplated by the present subject matter includes removing the device from storage and inserting a male terminal into the body of the implantable medical device. Some of these embodiments include coupling the male terminal to the body of the device by tightening the fastener against the male terminal.

Additional processes contemplated by the present subject matter include applying a lubricant to the slit. Examples of lubricants contemplated by the present subject matter include, but are not limited to, MDX4-4159, NuSil MED420, MED-4159, MED-4162, MED1-4162, and/or NUSIL, and combinations thereof. NUSIL is a registered trademark of NUSIL TECHNOLOGY headquartered in Carpinteria, Calif., USA. MDX4-4159, NuSil MED420, MED-4159, MED-4162, MED1-4162 each are manufactured by DOW CORNING, which is headquartered in Midland, Mich., USA.

The present subject matter additionally contemplates bundling the implantable device with a torque limited driver for adjusting the fastener. In various embodiments, the torque driver is torque limited during tightening. In additional embodiments, the torque driver is torque limited during loosening. Torque drivers which are torque limited during tightening and loosening are additionally contemplated by the present subject matter. Embodiments are contemplated in which a non-torque limited driver is bundled with a device of the present subject matter.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. A system for fastening a male terminal with a driver, the system comprising:
   a body defining an at least partially threaded recess which intersects with a female recess sized to receive the male terminal;
   a fastener having an at least partially threaded body and a flanged head mateable with the driver, the fastener disposed at least partially in the at least partially threaded recess, the flange having a diameter which is larger than a diameter of the at least partially threaded recess; and
   a flexible septum coupled to the body and covering the at least partially threaded recess, the flexible septum including a portion defining an aperture sized for passage of the driver;
   wherein the flange of the fastener abuts the portion of the flexible septum defining the aperture, with the aperture open and sized for passage of the driver, and wherein the fastener is adapted to be fastened with the flange disposed against the body and flex closed the flexible septum, with the aperture closed and sealed.

2. The system of claim 1, wherein the aperture is a slit.

3. The system of claim 1, wherein the fastener has an unthreaded fastener portion disposed near a distal portion of the fastener, opposite the flange, the fastener to be disposed at least partially in the at least partially threaded recess.

4. The system of claim 1, wherein the flexible septum includes silicone.

5. The system of claim 1, wherein a distal portion of the fastener, opposite the flange, is substantially convex.

6. The system of claim 1, wherein the fastener includes a regular hexagonal recess adapted to couple to the driver.

7. The system of claim 6, wherein the regular hexagonal recess includes a slot.

8. The system of claim 1, wherein the body is part of an implantable, biocompatible device.

9. The system of claim 8, wherein the implantable, biocompatible device is a pacemaker.

10. The system of claim 8, wherein the implantable, biocompatible device is a cardioverter defibrillator.

11. The system of claim 2, wherein the fastener is disposed against the slit and the slit is open in a mode of operation.

12. The system of claim 11, further wherein the slit is lubricated with a lubricant.

13. The system of claim 1, wherein the fastener includes a set screw.

14. The system of claim 13, wherein the set screw includes the flange and a threaded portion.

15. The system of claim 14, wherein the set screw includes an unthreaded portion, with the threaded portion disposed between the flange and the unthreaded portion.

16. The system of claim 1, wherein cardiac rhythm management electronics are disposed in the body.

17. The system of claim 5, wherein the distal portion includes a bevel.

18. The system of claim 1, further comprising a cover defining the flexible septum.

19. The system of claim 18, wherein the cover is disposed in the body.

20. The system of claim 1, wherein the recess is cylindrical.

21. The system of claim 1, wherein the body is formed of a polymer.

* * * * *